(12) United States Patent
Roesch et al.

(10) Patent No.: US 10,633,313 B1
(45) Date of Patent: Apr. 28, 2020

(54) METHOD FOR MAXIMIZING THE VALUE OF GAS STREAMS CONTAINING CARBON MONOXIDE, CARBON DIOXIDE, AND HYDROGEN

(71) Applicant: L'Air Liquide, Société Anonyme pour l'Etude et l'Exploitation des Procédés Georges Claude, Paris (FR)

(72) Inventors: Alexander Roesch, Frankfurt am Main (DE); Joseph T. Stroffolino, IV, Pearland, TX (US)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 16/366,033

(22) Filed: Mar. 27, 2019

(51) Int. Cl.
*C07C 29/151* (2006.01)
*C01B 3/56* (2006.01)

(52) U.S. Cl.
CPC ............ *C07C 29/1518* (2013.01); *C01B 3/56* (2013.01); *C01B 2203/042* (2013.01); *C01B 2203/0475* (2013.01); *C01B 2203/061* (2013.01)

(58) Field of Classification Search
CPC ......... C07C 31/04; C07C 29/151; C01B 3/12; C01B 3/52; C01B 3/56; C01B 3/506; C01B 2203/062; C01B 2203/063; C01B 2203/065; C01B 2203/061; C01B 2203/0475; C01B 2203/0435; C01B 2203/0415; C01B 2203/0283; C01B 2203/0146; Y02C 10/12
See application file for complete search history.

(56) References Cited

U.S. PATENT DOCUMENTS

2006/0149423 A1\* 7/2006 Barnicki .................... C10J 3/00
700/286
2015/0152030 A1\* 6/2015 Trott ......................... C01B 3/12
518/704

\* cited by examiner

*Primary Examiner* — Jafar F Parsa
(74) *Attorney, Agent, or Firm* — Elwood L. Haynes

(57) ABSTRACT

A method for maximizing the value of gas streams containing carbon dioxide, carbon monoxide, and hydrogen including splitting a carbon dioxide, carbon monoxide, and hydrogen containing stream into a first fraction and a second fraction, introducing at least a portion of a scrubbed first fraction into a temperature swing adsorption unit to further remove carbon dioxide and to remove water, separating at least a portion of the scrubbed and dried first fraction to produce a carbon monoxide product stream and a hydrogen product stream, combining at least a portion of the hydrogen product stream and the second fraction to produce a methanol-synthesis gas stream, wherein at least a portion of a crude methanol stream, generated after a single pass through the methanol synthesis reactor, is withdrawn and used as a crude methanol product, and wherein the methanol-synthesis gas stream is produced without utilizing a water gas shift reaction.

20 Claims, 2 Drawing Sheets

METHOD FOR MAXIMIZING THE VALUE OF GAS STREAMS CONTAINING CARBON MONOXIDE, CARBON DIOXIDE, AND HYDROGEN

BACKGROUND

As the various chemical and petrochemical facilities work to produce useful industrial gases, they inevitably also produce off gases or waste gas streams. Often these waste gas streams consist of components that can be valorized under the proper conditions. It is the intent of the instant application to maximize the value of such waste gas streams, particularly those containing carbon dioxide, carbon monoxide and hydrogen.

SUMMARY

A method for maximizing the value of gas streams containing carbon dioxide, carbon monoxide, and hydrogen including splitting a carbon dioxide, carbon monoxide, and hydrogen containing stream into a first fraction and a second fraction, introducing at least a portion of a scrubbed first fraction into a temperature swing adsorption unit to further remove carbon dioxide and to remove water, separating at least a portion of the scrubbed and dried first fraction to produce a carbon monoxide product stream and a hydrogen product stream, combining at least a portion of the hydrogen product stream and the second fraction to produce a methanol-synthesis gas stream, wherein at least a portion of a crude methanol stream, generated after a single pass through the methanol synthesis reactor, is withdrawn and used as a crude methanol product, and wherein the methanol-synthesis gas stream is produced without utilizing a water gas shift reaction.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
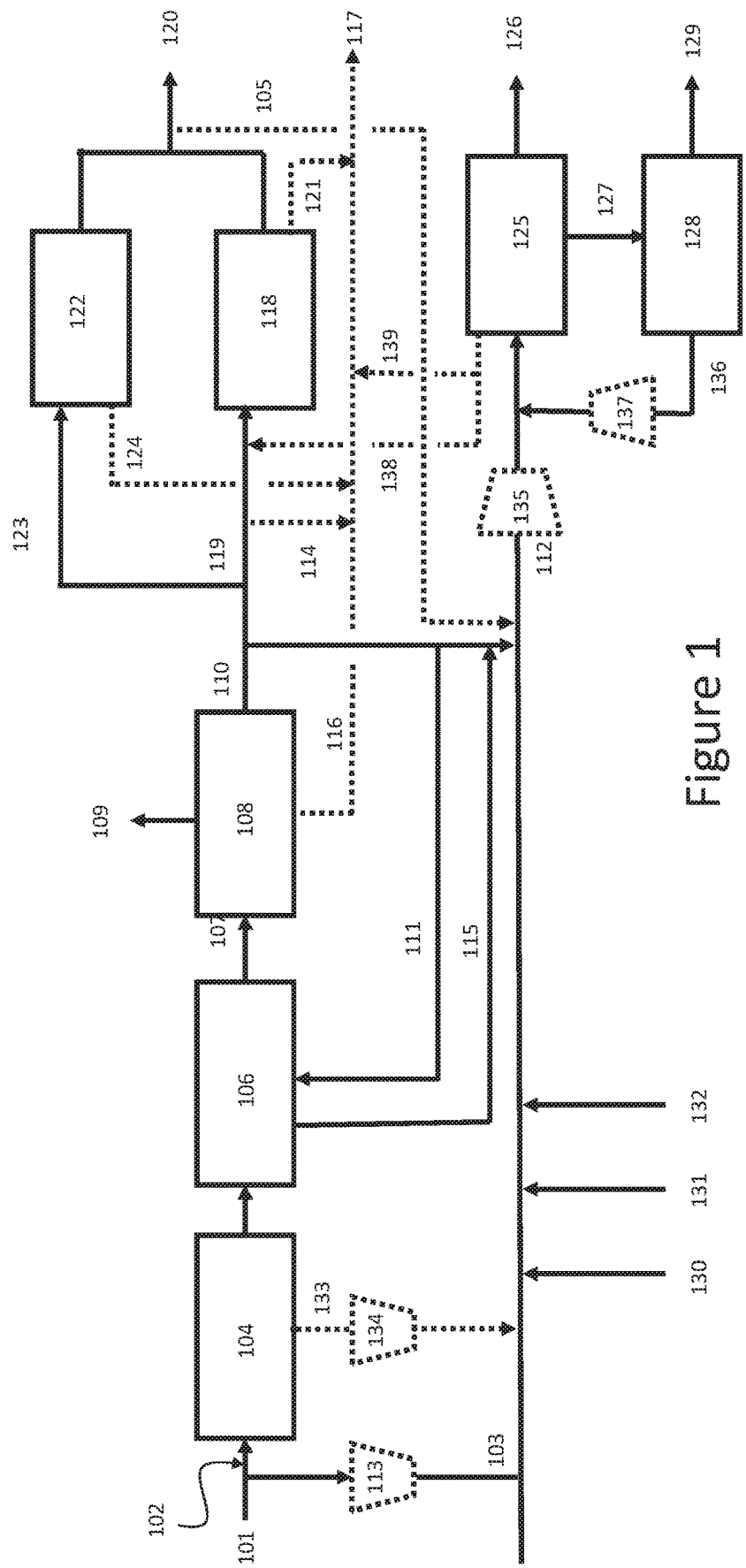
FIG. 1 is a schematic representation of the process side, in accordance with one embodiment of the present invention.

Turning to FIG. 1, feed gas stream 101, composed mainly of carbon monoxide and hydrogen, but which may also contain other components, may be compressed (not shown) and if required, may be purified by any means known to the art, for example catalytically (not shown) to remove undesirable components such as any oxygen, sulfur, unsaturated hydrocarbons, or other impurities in the stream. Other feed gases may include carbon dioxide rich streams 130, hydrogen rich streams 131, or carbon monoxide rich streams 132 at varying levels of composition.

In one embodiment of the current invention, a target product carbon monoxide 109 amount is established. In order to obtain this target, feed gas stream 101 is divided into at least a first fraction 102 and a second fraction 103. In this process, neither first fraction 102 nor second fraction 103 enters a water gas shift reaction at any point. First fraction 102 is sent to carbon dioxide removal system 104 followed by temperature swing adsorption Unit 106 which removes any residual carbon dioxide and moisture. Feed gas stream 101 may be compressed prior to being split into first fraction 102 and second fraction 103. Carbon dioxide removal system 104 may be a molecular sieve system, a membrane system, an amine scrubber, an activated carbon scrubber, or any system known in the art.

Scrubbed and dried first fraction 107 is then separated 108 into high purity carbon monoxide product stream 109 and hydrogen-rich gas stream 110. The separation process may be cryogenic. Cryogenic separator 108 may be a methane wash system, a partial condensation system, or any system known in the art. Residual gas 116 from cryogenic separator 108 may be sent to the battery limit and may be used as fuel.

A portion 111 of hydrogen-rich gas stream 110 may be used for regenerating and or purging temperature swing adsorption unit 106 and afterward, may be returned 115 to hydrogen-rich gas stream 110. A portion 119 of hydrogen-rich gas stream 110 may be used to generate high purity hydrogen product stream 120 by means of pressure swing adsorption 118. Residual gas 121 from pressure swing adsorber 118 may be sent to the battery limit and may be used as fuel. A portion 123 of hydrogen-rich gas stream 110 may be used to generate high purity hydrogen product stream 120 by means of membrane unit 122. Residual gas 124 from membrane unit 122 may be used as fuel or recycled within the facility. If no high purity hydrogen product stream 120 is desired, remaining hydrogen-rich gas stream 114 may be sent to the battery limit and may be used as fuel.

Second fraction 103 may be compressed 113 if necessary. Second fraction 103 may be combined with a carbon dioxide stream which may be either imported from the battery limit carbon dioxide rich gas import stream 130, or recycled 132 from the $CO_2$ removal system by means of an optional compressor 133. Second fraction 103 may be combined with hydrogen rich gas import stream 131, which may be introduced from outside the system. Second fraction 103 may be combined with carbon monoxide rich gas import stream 132, which may be introduced from outside the system. With the exception of the potential for the addition of streams 130, 131, and/or 132, second fraction 103 is otherwise untreated. Second fraction 103 is mixed with a portion of the hydrogen-rich gas stream 110 (or alternatively, at least a portion 105 of high purity hydrogen product stream 120) to achieve methanol synthesis gas stream 112 having the desired stoichiometric number (SN) defined as $(H_2-CO_2)/(CO+CO_2)$ for methanol production.

Methanol synthesis gas stream 112 enters methanol synthesis reactor loop 125 which may be achieved by a compressor 135. Crude methanol stream 127 generated after a single pass is separated and sent to methanol distillation Unit 128. Synthesis gas 136 remaining after crude methanol separation 128 may be compressed 137 back to the front of the synthesis loop 125. Purge stream 138 from the loop may be required to control inerts. Purge stream 138 is hydrogen rich and at a high pressure and may be recycled back to the hydrogen rich gas import stream 119 entering the pressure swing adsorber 118. Alternatively purge steam 139 may be used as fuel.

Crude methanol stream 127 from methanol synthesis loop reactor 125 may be flashed and distilled with reboiling media in methanol distillation Unit 128, to achieve high purity methanol product stream 129, having a higher purity than crude methanol stream 127. Alternatively, crude methanol from methanol synthesis reactor loop 125 may be exported as the crude methanol product stream 126.

Figure 2:
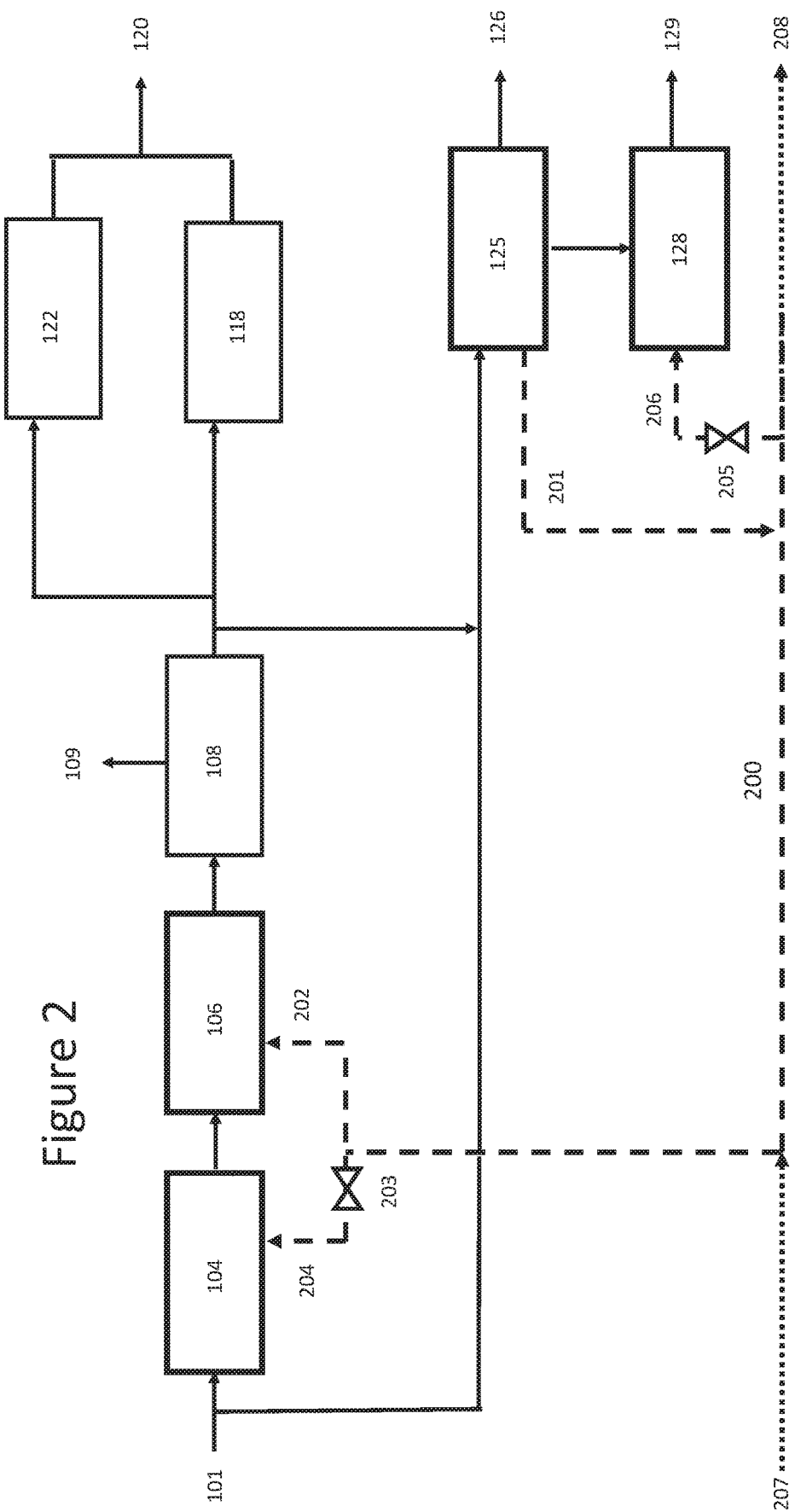
FIG. 2 is a schematic representation of the process side and the steam side, in accordance with one embodiment of the present invention.

Turning to FIG. 2, steam system 200 is illustrated, via dashed lines. Saturated medium pressure steam 201 is generated during the methanol reaction.

As used herein, the term "medium pressure steam" is defined as saturated steam with pressures between 400 psig and 650 psig (temperatures between 450 F and 500 F). Preferably with pressures between 400 psig and 600 psig (temperatures between 450 F and 490 F). More preferably with a pressure of 580 psig and a temperature of 480 F.

As used herein, the term "low pressure steam" is defined as saturated steam with pressures between 15 psig and 50 psig (temperatures between 250 F and 300 F). Preferably with pressures between 30 psig and 50 psig (temperatures between 275 F and 300 F). More preferably with a pressure of 40 psig and a temperature of 286 F.

Saturated medium pressure steam 201 may be reduced in pressure by way of pressure reduction valves 203/205. The reduced pressure (low pressure) steam may be used as reboiling media 204 for the $CO_2$ removal system 104. Low pressure steam 206 may be used as reboiling media within the methanol distillation unit 128, if applicable.

If more steam 201 is generated within the methanol synthesis reactor 125 than required for heating or other uses within the system, or a more efficient or economical external source 207 of steam exists, steam may be exported 208. If more steam demand exists than is generated within the methanol synthesis reactor 125, steam required for heating or other uses within the system, may be imported 207.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method maximizing the value of gas streams containing carbon dioxide, carbon monoxide, and hydrogen, the method comprising:
   splitting a carbon dioxide, carbon monoxide, and hydrogen containing stream into a first fraction and a second fraction,
   scrubbing at least a portion of the first fraction in a carbon dioxide removal system to remove at least a portion of the carbon dioxide,
   introducing at least a portion of the scrubbed first fraction into a temperature swing adsorption unit to further remove carbon dioxide and to remove water,
   separating at least a portion of the scrubbed and dried first fraction to produce a carbon monoxide product stream and a hydrogen product stream,
   combining at least a portion of the hydrogen product stream and the second fraction to produce a methanol-synthesis gas stream, and
   introducing at least a portion of the methanol-synthesis gas stream into a methanol synthesis reactor,
   wherein at least a portion of a crude methanol stream, generated after a single pass through the methanol synthesis reactor, is withdrawn and used as a crude methanol product, and
   wherein the methanol-synthesis gas stream is produced from a carbon monoxide and hydrogen containing stream without utilizing a water gas shift reaction.

2. The method of claim 1, wherein the second fraction does not pass through a scrubber prior to combining with the first fraction.

3. The method of claim 1, wherein the carbon monoxide and hydrogen containing stream is not hydrogenated.

4. The method of claim 1, wherein the scrubbed and dried first fraction is cryogenically separated to produce a carbon monoxide product stream and a hydrogen product stream.

5. The method of claim 1, wherein at least a portion of the hydrogen rich stream is introduced into the temperature swing adsorption unit during regeneration.

6. The method of claim 1, wherein the cryogenic separation further produces a residual gas stream, and wherein at least a portion of the residual gas stream is used as a fuel gas product.

7. The method of claim 1, further comprising combining a carbon dioxide-rich gas import stream with the second fraction.

8. The method of claim 1, further comprising combining a hydrogen product gas import stream with the second fraction.

9. The method of claim 1, further comprising combining a carbon monoxide-rich import gas stream with the second fraction.

10. The method of claim 1, further comprising a pressure swing adsorption unit downstream of the cryogenic separation, wherein at least a portion of the hydrogen product stream is treated in the pressure swing adsorption unit to produce at least a portion of the hydrogen product stream.

11. The method of claim 10, wherein the pressure swing adsorption unit produces a tail gas stream, and wherein at least a portion of the tail gas stream is used as a fuel gas product.

12. The method of claim 1, further comprising a membrane separation unit downstream of the cryogenic separation, wherein at least a portion of the hydrogen product stream is treated in the membrane separation unit to produce at least a portion of hydrogen product stream.

13. The method of claim 1 wherein the membrane separation unit produces a residual gas stream, and wherein at least a portion of the residual gas stream is used as a fuel gas product.

14. The method of claim 1, wherein at least a portion of a crude methanol stream, generated after a single pass through the methanol synthesis reactor, is withdrawn and purified in a methanol distillation unit, and used as pure methanol product.

15. The method of claim 14, further comprising introducing medium pressure steam generated in the methanol synthesis reactor into a steam system and reducing the pressure of at least a portion of the steam in the steam system and introducing the reduced pressure steam into the methanol distillation unit as reboiling media.

16. The method of claim 1, further comprising introducing medium pressure steam generated in the methanol synthesis reactor into a steam system.

17. The method of claim 16, further comprising introducing at least a portion of the steam in the steam system into the temperature swing adsorption unit during a regeneration cycle.

18. The method of claim 16, further comprising reducing the pressure of at least a portion of the steam in the steam system and introducing the reduced pressure steam into the carbon dioxide removal system as reboiling media.

19. The method of claim 16, further comprising importing medium pressure steam into the steam system when an overall steam demand exceeds the medium pressure steam generated in the methanol synthesis reactor.

20. The method of claim 16, further comprising exporting medium pressure steam from the steam system when an overall steam demand is exceeded by the medium pressure steam generated in the methanol synthesis reactor.

\* \* \* \* \*